United States Patent [19]

Sanchez, Jr.

[11] Patent Number: 5,449,004
[45] Date of Patent: Sep. 12, 1995

[54] BIRTHING GOWN

[76] Inventor: Esberto J. L. Sanchez, Jr., 4585 Grove St., Apt. 4, West Palm Beach, Fla. 33415

[21] Appl. No.: 362,173

[22] Filed: Dec. 22, 1994

[51] Int. Cl.⁶ .................. A61G 15/00; A61G 1/00; A61F 5/37
[52] U.S. Cl. .................. 128/845; 128/846; 128/875; 224/158
[58] Field of Search .......... 128/845, 846, 869, 874, 128/875; D3/31; 224/158, 222, 267; 2/114

[56] References Cited

U.S. PATENT DOCUMENTS

| 982,376 | 1/1911 | MacFarlane | 224/158 |
|---|---|---|---|
| 2,030,091 | 2/1936 | Behringer | 2/114 |
| 2,851,033 | 9/1958 | Posey | 128/845 |
| 4,817,836 | 4/1989 | Bates | 224/158 |
| 4,823,418 | 4/1989 | Downs | 5/82 R |
| 5,027,832 | 7/1991 | Williams | 128/849 |
| 5,056,533 | 10/1991 | Solano | 128/845 |
| 5,246,152 | 9/1993 | Dotseth | 224/158 |
| 5,287,860 | 2/1994 | Owens | 128/851 |
| 5,337,427 | 8/1994 | Pagano | 128/845 |

Primary Examiner—Michael A. Brown
Attorney, Agent, or Firm—McHale & Slavin

[57] ABSTRACT

A birthing gown that is placed around the neck of a birthing assistant having sleeves or through holes available for placement of the birthing assistant's biceps and forearms so as to allow the birthing gown to be simply worn as a garment protector or transformed into a birthing cradle. Attachments are provided for insertion of the birthing assistant's thumb so as to prevent slippage of the birthing cradle as well as provide the ability to move a newborn child without grasping of the child with a human hand until mucous fluid of the newborn child has been removed.

13 Claims, 2 Drawing Sheets

BIRTHING GOWN

FIELD OF THE INVENTION

The present invention relates generally to the support of a child upon birth, and more particularly, to a birthing gown that is worn around a birthing assistant's neck and can be used to form a birthing cradle for support and transfer of a child upon birth.

BACKGROUND OF THE INVENTION

It is commonly known that during childbirth a newborn child can be easily dropped. Childbirth is a process in which a child is expelled from the uterus of a woman through a birth canal. During childbirth, the woman is subjected to contractions of the uterus commonly referred to as labor. As labor progresses the contractions increase in frequency and severity. While giving birth a woman is typically assisted by at least one person who directs the child through the last section of the birth canal and is available for supporting the child upon delivery. As the woman is subjected to disabling contractions throughout the duration of labor, she is typically incapable of providing assistance in support of the child. Further, in many cases the woman prefers anesthesia to alleviate the pain which has a side effect of lessening the woman's alertness.

The problem in delivery is that the birthing assistant must not only attend to the comfort of the woman but must further assist in safely directing the child into the world. However, the child is born with a fluid secreted from the woman's mucous membranes that moistens and protects the skin of the newborn child. Mucous is a thick slimy secretion which makes the child extremely slippery and difficult to hold. Should the birth assistant utilize latex gloves or the like material, the fluid operates with the gloves resulting in an extreme condition. Thousands of babies are dropped by birthing assistants including highly trained medical personnel, all to the detriment of the newborn. The cause may be a combination of slippery surfaces or inattention while trying to assist during delivery. In other instances, the child is grasped so firmly to prevent dropping that the child can be easily bruised. In any event, the fall of a child can result in a severe injury, physically to the child and mentally to the birthing parent.

For these reasons various attempts have been made to correct the problem including the use of hospitals requiring at least two birthing assistants during delivery. Support drapes such as that disclosed in U.S. Pat. No. 5,027,832 set forth a version of a commonly used drape capable of retaining fluid as well as preventing the fall of a child during birth.

U.S. Pat. No. 5,287,860 discloses a birthing drape used primarily for catching body fluids expelled during child birth by use of a catch basin that is placed below the body of the birthing mother and hooked over each of the woman's extended legs.

U.S. Pat. No. 4,823,418 discloses a birth safety net directed to preventing the dropping of a newborn child by use of a five cornered net which is coupled to a portion of the birthing chair or birthing bed. The problem with this disclosure is that the device must be attached to a special table and is used only as a safety net. Thus, the birthing assistant must still pick up the child leaving no "safety net" during the movement of the child. Finally, the use of birthing chairs and beds is archaic and seldom practiced.

Thus, what is needed in the art is a device that can be used during childbirth so as to provide a safety net to prevent a newborn child from falling and can be used in transferring of the child from one position to another.

SUMMARY OF THE INVENTION

The instant invention is a birthing gown that can be worn by the birthing assistants. The gown is positioned over the front of the person and is secured to the person's neck in such a manner that it cannot become dislodged. During childbirth the gown may operate to prevent fluids from spoiling the garments of the assisting personnel but more importantly, used to correctly position the assisting personnel during delivery. In operation the gown is secured to the neck of a birthing assistant and a free end of the birthing gown is placed beneath the birthing mother or hooked to attachment fasteners on the birthing table. During delivery the birthing assistants are free to use their arms to assist during birth and may rely upon the gown to provide emergency support for the child. Upon delivery, the child is placed onto the gown which then operates as a birthing cradle. Arm attachment holders are provided to turn the gown into a cradle with the free end now available as thumb loops allowing the person to have free hands yet fully support the child for transfer.

An alternative embodiment of the instant invention allows the assisting personnel to place their arms through the birthing gown which provides a lower cost of manufacture but maintains the ability to have free hands for directing the child into the formed birthing cradle. Attachments to the neck, biceps and forearms forms the support for the birth cradle as well as eliminates the possibility of delivery personnel squeezing when trying to prevent the child from slipping and allows those having inadequate hand strength to assist in holding of a child.

Thus, an objective of the instant invention is to provide a birthing gown that operates as a safety net during delivery, forms into a birthing cradle, and allows for the safe transportation of a newborn child.

Another objective of the instant invention is to provide a birthing gown that allows the delivery personnel to assist in childbirth by the use of free hand movement.

Still another objective of the instant invention is to provide a means for transferring a newborn child's weight to the shoulders and arms of a birthing assistant to accommodate a person having inadequate hand strength.

Yet still another objective of the instant invention is to provide a drape so as to aid in directing body fluids from the woman into the birthing cradle.

Another objective of the instant invention is to provide a birthing gown that can be worn by all of the delivery personnel so as to prevent the spoiling of clothing yet provide each person with the ability to act as a transferring person and force the proper positioning of at least one person during delivery.

Other objectives and advantages of this invention will become apparent from the following detailed description taken in conjunction with the accompanying drawings wherein are set forth, by way of illustration and example, certain embodiments of this invention. The drawings constitute a part of this specification and include exemplary embodiments of the present inven-

DETAILED DESCRIPTION OF THE PREFERRED EMBODIMENT

Although the invention is described in terms of a specific embodiment, it will be readily apparent to those skilled in this art that various modifications, rearrangements and substitutions can be made without departing from the spirit of the invention. The scope of the invention is defined by the claims appended hereto.

Figure 1:
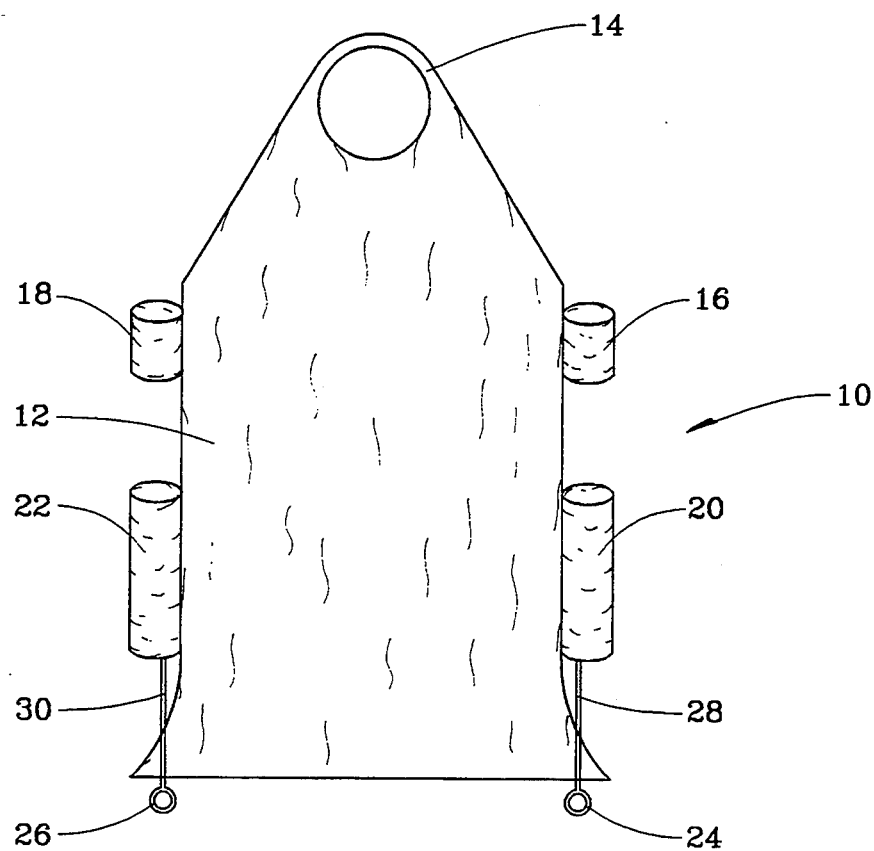
FIG. 1 is a top plane view of the preferred embodiment of the instant invention.

Now referring to FIG. 1 shown is a top plane view of the birthing gown 10 of the instant invention. The gown 10 consists of a substantially rectangular shaped base section 12 constructed from cotton, nylon, lycra, plastic or the like flexible material. The base support section 12 is defined by a first end, a second end and two spaced apart side edges disposed therebetween with two side surfaces all of which forms into a birthing cradle.

The first end leads to a neck hoop insertion 14 section which can be integrated into the support section 12 or consist of a neck hoop attachment 14 that is placed over a person's head for positioning around their neck. The neck hoop insertion 14 is preferably a circular device that will not loosen or become dislodged from the neck providing a means for securing around the neck of a birthing assistant. Alternatively, the neck portion may be a component tied or fastened around the neck with a primary objection of being able to transfer the weight of a child to the shoulders of the person yet maintain sufficient securement so as to prevent premature release.

Along each side edge of the birthing cradle is a means for coupling the base 12 to the arms of the birthing assistant. Left 16 and right 18 bicep connectors allow insertion of the upper arms of the person forcing the gown to be positioned parallel to the chest by directing the gown from the neck portion downward to the natural positioning of the biceps. The bicep connectors may use elasticity so as to accommodate various sized upper arms but need only provide sufficient room for insertion of the arms. Forearm attachment is provided by left sleeve 20 and right sleeve 22 which allow outward extension of the forearm, positioning the basis for the birthing cradle along a horizontal plane.

The biceps and forearm sleeves may be of a single piece with an articulation point therebetween allowing the birthing cradle to conform to the shape of the particular person's arms. Separate arm connectors allow the use of the gown for various size personnel wherein the elbows can be positioned between the biceps and forearm coupling sections.

Along each corner of the free end of the birthing cradle 12 is located attachment hoops 24 and 26 for coupling to a birthing bed or for attachment to the wearer's thumbs. When the gown is used to catch fluid or as a safety net, the attachment points 24 and 26 can be coupled to the birthing table allowing complete mobility of birthing assistant's arms by means of a direct connection to the birthing table. Before delivery the birthing assistant may place their arms in position so as to provide support for the child wherein the hands remain free to help place the child into position. The hooks may then be placed over the birthing assistant's thumbs to prevent the cradle from sliding up the arm. When the birthing gown is not in use, straps 28 and 30 may be used to secure the gown behind the wearer's back to operate as a protective gown for clothing.

Figure 2:
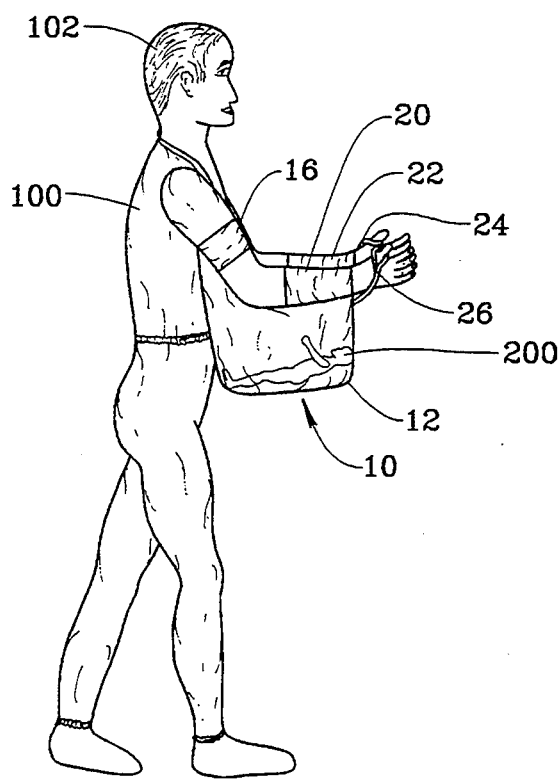
FIG. 2 is a perspective view of the instant invention in use as a birthing cradle.

Now referring to FIG. 2 depicted is a person 100 having the instant invention 10 placed around their neck and coupled to their arms with bicep connectors 16 and 18 and forearm connectors 20 and 22. In this embodiment the birthing cradle 12 is formed by use of the biceps to form a back to the cradle and the forearms providing a support for the base. Attachment hooks 24 and 26 are placed over the wearer's thumbs 104 and 106 to prevent the cradle from sliding up the arms. Child 200 is positioned between the arms and allowed to rest comfortably within the birthing cradle. The person's hands are shown in a free position extending beyond the cradle length so as to operate as bumpers should the person inattentively walk into an object thus protecting the child's body. Further the design prevents the operator from grasping the baby with excessive force to overcome the skin surface immediately after child birth. Once the child has been cleaned of the mucous fluid, the operator can lightly grasp the child without fear of sudden movement which would otherwise cause the infant to drop. Proper positioning of the birthing cradle operates to position a majority of the weight about the shoulder of the birthing assistant which is imperative in clinics where a birthing assistant may be exhausted from multiple births.

Figure 3:
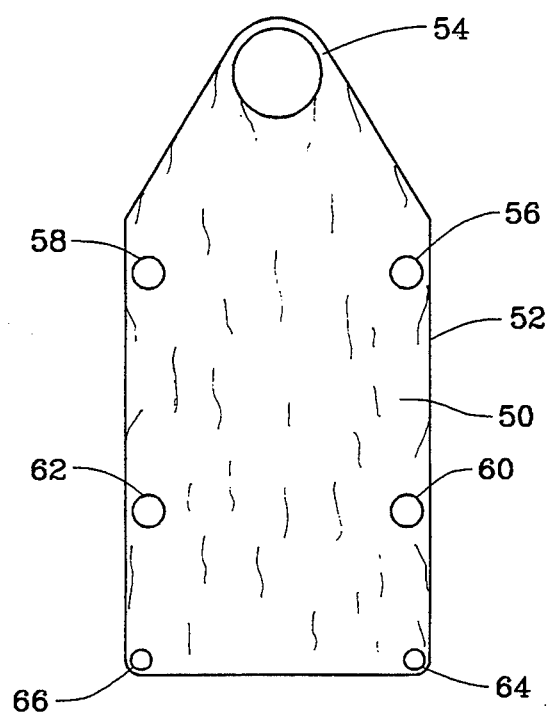
FIG. 3 is a top plane view of an alternative embodiment to the instant invention.

FIG. 3 is an alternative embodiment of the instant invention having a simplified construction consisting of a single sheet of material such as nylon, cotton, lycra, plastic, spandex, or silk 50 which has a reinforced perimeter edge 52 leading to a neck hole 54. Through holes 56 and 58 are provided for the biceps as are through holes 60 and 62 for the forearms. Through holes 64 and 66 provide thumb loop attachments which can further be used to attach to the birthing table. This embodiment provides a low cost alternative to the birthing gown as the bicep and forearm sleeves are replaced with reinforced through holes eliminating a major cost of sleeve construction during manufacture. The intent of the invention is not altered as both embodiments provide a means for preventing a newborn child from dropping, as well as providing a means for transferring the child without human hand contact.

If an expectant mother is a known carrier of aids, the birthing gown may be made of plastic so as to prevent contact with fluids. An open net design provides the birthing personnel with the ability to see through the gown during the delivery process. A cotton birthing gown will allow the operating personnel to reuse the gown upon cleaning and sterilization.

Figure 4:
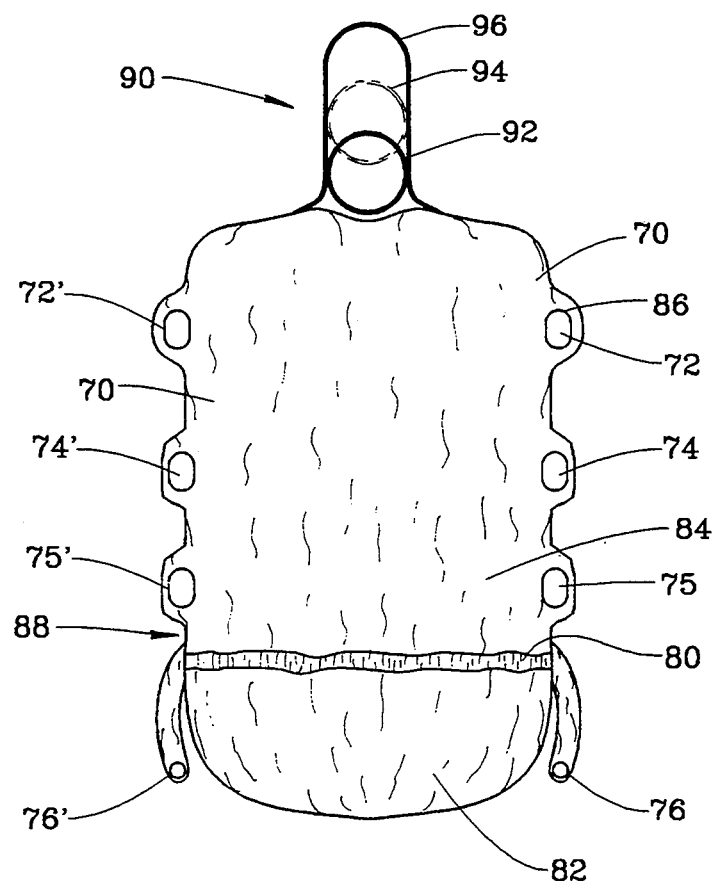
FIG. 4 is a top plane view of an alternative embodiment.

Now referring to FIG. 4 is an embodiment of the instant invention having a body portion 70 consisting of a single sheet of material with through holes 72 provided for insertion of a carrier's arm as well as adjoining arm holes 74 allowing the operator to weave their upper and lower arm into position as previously described for connection to thumb fastener loops 76 and 78. In this embodiment a flexible band strap 80 sets forth a pouch 82 which operates to catch fluids. This embodiment sets forth a separating line 84 which distinguishes the position for a child between an upper vertical surface 86 and a lower horizontal surface 88. In operation, a child placed on the lower surface 88 would be held at a substantially horizontal plane wherein excess fluid would flow into the formed pouch 82 with expansion flex band 80 preventing accidental droppage of the child should the operator's arms become so weak as not be able to maintain the surface 88 horizontally. The weight of the child will depress the horizontal surface 88 while the expansion flex band maintains sufficient resiliency so as to form the pouch.

Height adjustment collars provide the device with the ability to be used with personnel of various heights. The user simply chooses which height adjustment collar is suitable for their use and places their neck through opening 92, 94, or 96. The solid adjustment collar is deemed necessary in most instances in light of the fragile cargo to be carried. As provided by this embodiment should the operator's arms become too weak to carry the child, the adjustment collar must be able to support the child entirely if the child falls into the pouch 82 when the operator's arms are placed at their side.

It is to be understood that while I have illustrated and described certain forms of my invention, it is not to be limited to the specific forms or arrangement of parts herein described and shown. It will be apparent to those skilled in the art that various changes may be made without departing from the scope of the invention and the invention is not to be considered limited to what is shown in the drawings and described in the specification.

What I claim is:

1. A birthing gown that forms into a birthing cradle comprising: a base formed from a rectangular sheet of flexible material defined by a first end, a second end and two spaced apart side edges disposed therebetween, said sheet having two side surfaces; means for securing said first end around the neck of a birthing assistant; and a means for coupling said side edges to the arms of the birthing assistant; whereby said base sheet is secured to the birthing assistant's neck allowing the base to be used as a gown wherein the coupling of said base sheet to the arms of the birthing assistant forms a cradle for support and transfer of a newborn child.

2. The birthing gown according to claim 1 wherein said means for securing is further defined as a throughhole disposed along said first end sized for placement over the head of a birthing assistant.

3. The birthing gown according to claim 1 wherein said means for coupling is further defined as a pair of bicep sleeves disposed on opposite side edges of said base and a pair of forearm sleeves disposed along opposite side edges of said body portion.

4. The birthing gown according to claim 1 including two spaced apart hoops disposed along said second end of said base.

5. The birthing gown according to claim 4 including a means for securing said hoops around the body of the assistant.

6. The birthing gown according to claim 1 wherein said means for securing said first end around the neck of a birthing assistant is adjustable.

7. The birthing gown according to claim 1 wherein said material is transparent.

8. The birthing gown according to claim 1 wherein said material is impervious to fluids.

9. The birthing gown according to claim 1 including a pouch formed by overlapping said sheet of flexible material forming a free edge having an elastic means.

10. A birthing gown that forms into a birthing cradle comprising: a base formed from a rectangular sheet of flexible material defined by a first end, a second end and two spaced apart side edges disposed therebetween, said sheet having two side surfaces; at least one centrally disposed throughhole juxtapositioned to said first end for securing around the neck of a birthing assistant; a plurality of spaced apart throughholes disposed along each side edge of said base sheet; whereby said base sheet is secured to the birthing assistant's neck by placement of said first centrally disposed throughhole over the assistant's neck allowing the base to be used as a gown wherein the insertion of the assistants' arms through said first pair of spaced apart throughholes by an upper surface of said side surface and insertion of the assistant's arms through said second pair of spaced apart throughholes by a lower surface of said side surface forming a cradle for support and transfer of a newborn child.

11. The birthing gown according to claim 10 including two spaced apart hoops disposed along said second end of said base.

12. The birthing gown according to claim 11 wherein said hoops are available for securement to a birthing table.

13. The birthing gown according to claim 10 including a pouch formed by overlapping said sheet of flexible material forming a free edge having an elastic means.

* * * * *